United States Patent
Shekarriz et al.

(10) Patent No.: US 7,178,380 B2
(45) Date of Patent: Feb. 20, 2007

(54) VIRTUAL IMPACTOR DEVICE WITH REDUCED FOULING

(75) Inventors: Alireza Shekarriz, Lake Oswego, OR (US); Robert Reed Moore, Ridgefield, WA (US); Joseph G. Birmingham, Vancouver, WA (US)

(73) Assignee: Joseph Gerard Birmingham, Vanconver, WA (US)

( * ) Notice: Subject to any disclaimer, the term of this patent is extended or adjusted under 35 U.S.C. 154(b) by 192 days.

(21) Appl. No.: 11/041,823

(22) Filed: Jan. 24, 2005

(65) Prior Publication Data

US 2006/0162424 A1    Jul. 27, 2006

(51) Int. Cl.
*G01N 1/00* (2006.01)
(52) U.S. Cl. .................................... 73/28.04
(58) Field of Classification Search ............. 73/863.22, 73/863.23, 28.01, 28.04, 28.05, 28.06, 863.21; 55/434; 65/267; 209/132
See application file for complete search history.

(56) References Cited

U.S. PATENT DOCUMENTS

| | | | | |
|---|---|---|---|---|
| 2,047,568 A | * | 7/1936 | Lissman | 209/135 |
| 2,570,129 A | * | 10/1951 | Johnson | 73/147 |
| 3,001,402 A | * | 9/1961 | Koblin | 73/863.21 |
| 3,104,680 A | * | 9/1963 | Orlin | 138/45 |
| 3,972,226 A | * | 8/1976 | Rountree et al. | 73/28.05 |
| 4,767,524 A | | 8/1988 | Yeh et al. | |
| 4,806,150 A | * | 2/1989 | Alvarez et al. | 75/338 |
| 4,836,032 A | * | 6/1989 | Redus et al. | 73/861.04 |
| 4,872,972 A | * | 10/1989 | Wakabayashi et al. | 209/143 |
| 5,109,708 A | * | 5/1992 | Lawless | 73/863.11 |
| 5,183,481 A | * | 2/1993 | Felder | 95/29 |
| 5,858,043 A | * | 1/1999 | Geise | 55/462 |
| 5,876,187 A | | 3/1999 | Forster et al. | |
| 5,967,332 A | * | 10/1999 | Willeke | 209/132 |
| 6,010,554 A | | 1/2000 | Birmingham et al. | |
| 6,062,392 A | * | 5/2000 | Birmingham et al. | 209/143 |
| 6,094,997 A | * | 8/2000 | Lemonnier | 73/863.22 |
| 6,120,573 A | | 9/2000 | Call et al. | |
| 6,227,809 B1 | | 5/2001 | Forster et al. | |
| 6,290,065 B1 | | 9/2001 | Kenning et al. | |

OTHER PUBLICATIONS

Liu et al, Generating Particle Beams fo Contgrolled Dimensions and Divergence: I. Theory of Particle Motion in Aerodynamic Lenses and Nozzle Expansions, Aerosol Science and Technology 22:293-313 (1995).
TSI Particle Instruments Model 3801-030 Aerodyamic Focusing Lens Preliminary Information, 2003.

* cited by examiner

*Primary Examiner*—Hezron Williams
*Assistant Examiner*—John Fitzgerald
(74) *Attorney, Agent, or Firm*—Gary C. Cohn, PLLC (57) ABSTRACT

A virtual impactor device having reduced fouling includes injection ports within the separation zone to redirect particles that otherwise tend to impact the walls of the separation zone and produce fouling. The virtual impactor device preferably also includes an acceleration zone having concave and convex sections, which reduces fouling in that area. The virtual impactor device can be combined with various downstream components such as collectors, atomizers and various analytical devices.

44 Claims, 4 Drawing Sheets

VIRTUAL IMPACTOR DEVICE WITH REDUCED FOULING

BACKGROUND OF THE INVENTION

This invention relates to a virtual impactor type aerosol concentration or collection device.

Virtual impactor particle collection devices are well-known, being described, for example in U.S. Pat. Nos. 4,767,524, 6,010,554, 6,120,573 and 6,290,065, among others. Generally, these consist of an acceleration nozzle, in which the flow path is constricted in order to increase flow velocity, and a separation zone located downstream from the acceleration nozzle, where the fluid stream is split into at least two channels. A minor (in terms of fluid volume) flow travels more or less in the original direction of flow (i.e., the direction of flow through the constriction). The inertia of the particles causes most of them to be carried off with this minor flow. A major flow containing most of the fluid is taken off at an angle to the original direction of flow. The large inertia of the particles makes them less able to navigate this change in direction, and so this major flow contains a smaller particle concentration than either the original stream or the minor flow. The fluid containing the concentrated particles is then passed through a collector which removes the particles from the fluid. Virtual impactor type concentrators often have the further advantages that they require relatively low pressure drops, can be quite small in size, have low energy requirements, and are scalable.

Virtual impactor devices are highly prone to fouling due to collisions of the particles with the side walls of the device. These collisions can occur in the acceleration nozzle, in the separation zone, or both. The fouling problem is often so great that the virtual impactor device effectively functions like a filter, removing rather than concentrating the particles. As a result, many virtual impactor devices exhibit a concentration efficiency, defined as the ratio of particle concentration in the inlet fluid to that of the (supposedly) concentrated exit stream, of less than 1.0. So many of the particles become captured by the virtual impactor device that the exit streams often contain a lower concentration of particles than the starting fluid.

It is highly desirable to provide a virtual impactor device which is less prone to fouling and produces an effluent stream with a higher concentration of particles.

SUMMARY OF THE INVENTION

In one aspect, this invention is a virtual impactor device comprising an acceleration nozzle and a separation zone both aligned about a linear axis which defines a principal direction of aerosol flow through the device from the acceleration nozzle through the separation zone. The acceleration nozzle has a fluid inlet and a substantially narrower fluid outlet. The separation zone includes an inlet from the acceleration nozzle, a minor flow outlet downstream from the acceleration nozzle and oriented substantially along the linear axis, and at least one major flow outlet downstream from the acceleration nozzle and oriented at an angle to the linear axis. The minor flow outlet and the major flow outlet meet at a juncture, and a fluid injection port proximate to the juncture of the major flow outlet and the minor flow outlet is adapted to inject a fluid into the separation zone in a direction approximately opposite to that of the principal direction of aerosol flow though the impactor device.

In another aspect, this invention is a method for forming a fluid having an increased concentration of particles, comprising a) flowing a particle-laden fluid through a virtual impactor device, wherein the virtual impactor device includes an acceleration nozzle and a separation zone both aligned about a linear axis which defines a principal direction of aerosol flow through the device from the acceleration nozzle through the separation zone, the acceleration nozzle having a fluid inlet and a substantially narrower fluid outlet, and the separation zone including an inlet from the acceleration nozzle, a minor flow outlet downstream from the acceleration nozzle and oriented substantially along the linear axis; and at least one major flow outlet downstream from the acceleration nozzle and oriented at an angle to the linear axis, the minor flow outlet and the major flow outlet meeting at a juncture, and a fluid injection port proximate to the juncture of the major flow outlet and the minor flow outlet adapted to inject a fluid into the separation zone in a direction approximately opposite to that of the principal direction of aerosol flow though the impactor device;

b) injecting a fluid into the separation zone through the fluid injection port;

c) withdrawing a major flow depleted in the particles through the major flow outlet; and c) withdrawing a minor flow having an increased concentration in particles through the minor flow outlet.

In a preferred aspect, the major flow outlet and the separation zone inlet meet at an upstream juncture, and a second injection port residing proximate to the upstream junction is adapted to inject a fluid into the separation zone in a direction approximately in the principal direction of aerosol flow though the impactor device.

Injecting a fluid into the separation zone through the injection ports reduces fouling in the separation zone of the virtual impactor device. Although the invention is not limited to any theory, it is believed that the injected fluids direct the particle-laden fluid away from the interior surfaces of the separation zone, in effect helping to direct the fluid, together with the fluid-borne particles, toward the center of the major and minor flow outlets. This reduces the proportion of particles contacting the interior surfaces of the separation zone and thus reduces fouling.

In another aspect, this invention is an aerosol concentration device comprising an acceleration nozzle wherein 1) the acceleration nozzle comprises a conduit which narrows in a direction of aerosol flow from a fluid inlet into the aerosol concentration device towards the separation zone,
2) the acceleration nozzle includes a concave section in which the interior width of the acceleration nozzle decreases in the direction of aerosol flow; and
3) the acceleration nozzle includes a convex section downstream of the concave section, wherein the interior width of the acceleration nozzle further decreases in the direction of aerosol flow and through which the aerosol is directed through a nozzle outlet.

In the immediately preceding aspect, the aerosol concentration device preferably further comprises 4) a separation zone which includes an inlet from the acceleration nozzle, a minor flow outlet downstream from the acceleration nozzle and oriented substantially along the principle direction of flow; and at least one major flow outlet downstream from the acceleration nozzle and oriented at an angle to the principle direction of flow. The separation zone preferably is as described in the first aspect of the invention.

In yet another aspect, this invention is a method of concentrating particles contained in a fluid medium, comprising flowing the fluid medium through an aerosol concentration device under conditions such that a minor flow having an increased concentration of particles and at least one major flow having a reduced concentration of particles are produced, wherein the aerosol concentration device includes an acceleration nozzle wherein
1) the acceleration nozzle comprises a conduit which narrows in a principal direction of flow from a fluid inlet into the aerosol concentration device towards the separation zone,
2) the acceleration nozzle includes a concave section in which the interior width of the acceleration nozzle decreases in the principal direction of flow; and
3) the acceleration nozzle includes a convex section downstream of the concave section, wherein the interior width of the acceleration nozzle further decreases in the principal direction of flow and through which the aerosol is directed through a nozzle outlet.

Virtual impactor devices and acceleration nozzles of the invention are less prone to fouling due to collisions of particles with the interior surfaces. This allows for increased concentration efficiencies, longer useful life for the devices, reduced waste and reduced maintenance.

DETAILED DESCRIPTION OF THE INVENTION

Figure 1:
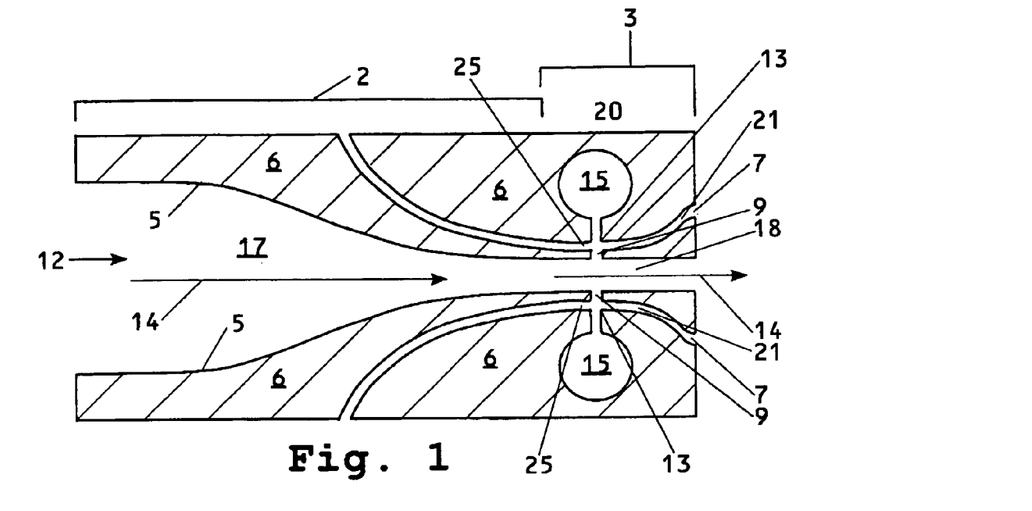
FIG. 1 is an enlarged side view, in section, of an embodiment of a virtual impactor device of the invention.

In FIG. 1, virtual impactor 1 includes an acceleration nozzle shown generally at 2 and a separation zone shown generally at 3. These are aligned along linear axis 14 which also defines a principal direction of flow through virtual impactor 1. Acceleration nozzle 2 includes walls 5 of block 6 which define conduit 17. Conduit 17 is in fluid communication with inlet 12, through which a particle-laden fluid enters virtual impactor 1. Conduit 17 decreases in width from inlet 12 in the principal direction of flow, which results in an acceleration of the fluid and particles as they pass through acceleration nozzle.

Separation zone 3 is in fluid communication with acceleration nozzle 2. Fluid (and particles) exiting acceleration nozzle 2 pass through inlet 10 into separation zone 3. Separation zone 3 includes minor flow outlet 18 and major flow outlets 9, each of which are downstream from acceleration nozzle 2. Minor flow outlet 18 is substantially aligned with the principal direction of flow of the particle-laden fluid as the fluid enters separation zone 3 from acceleration nozzle 2 through inlet 10. Major flow outlet 9 is oriented at an angle to that principle direction of flow. Because of the greater particle inertia, the particles tend to be unable to negotiate the change in direction required to travel into major flow outlet 9. Therefore, they exit through minor flow outlet 18 together with a portion of the fluid. The remainder of the fluid is taken off though major flow outlets 9 into conduits 15, where it is drawn off. Typically, most of the fluid is removed through major flow outlet 9, leaving a smaller volume, concentrated stream to exit through minor flow outlet 18.

Figure 3:
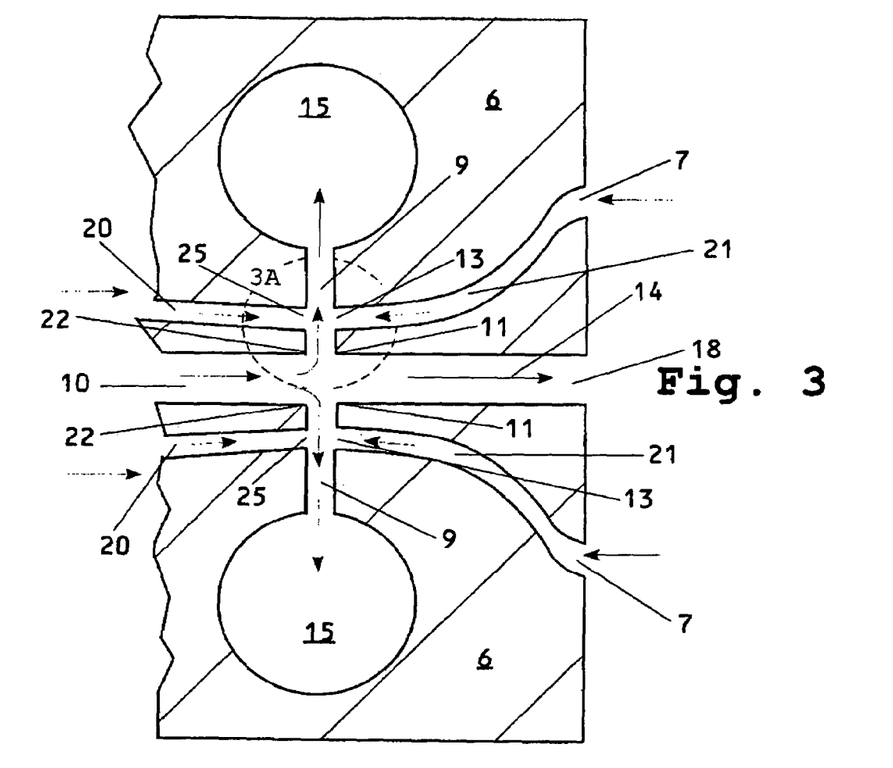
FIG. 3 is a further enlarged side view, in section, of the separation zone of a preferred embodiment of the invention.
Figure 3A:
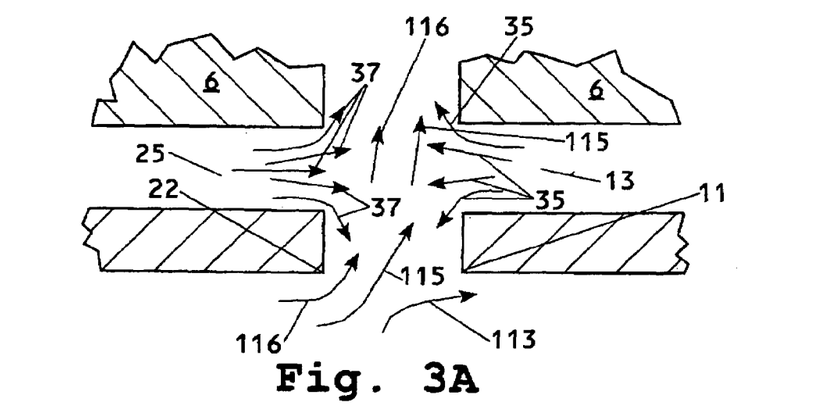
FIG. 3A is a still further enlarged, cross-sectional side view showing the manner of operation of an embodiment of the invention.

Major flow outlets and minor flow outlet 18 meet at junctures 11, as shown in FIGS. 3 and 3A. Fluid injection ports 13 reside proximate to junctures 11 and are adapted to inject a fluid into separation zone 3 in a direction approximately opposite of the principal direction of flow of the particle-laden fluid (indicated by arrow 14). As shown, fluid injection ports 13 are in fluid communication with conduits 21 and openings 7, so a fluid can be delivered through block 6 to fluid injection ports 13 through openings 7 and conduits 21.

Figure 2A:
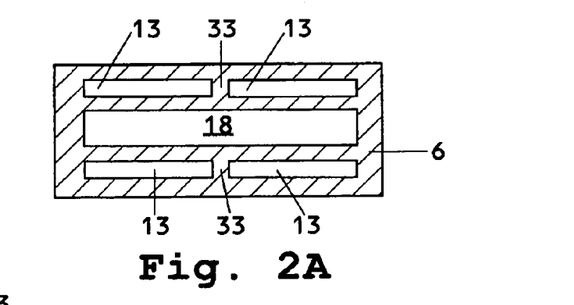
FIGS. 2A, 2B and 2C are further enlarged, cross-sectional views showing alternate arrangements of the fluid injectors and minor flow outlet ports of an embodiment of the invention.
Figure 2B:
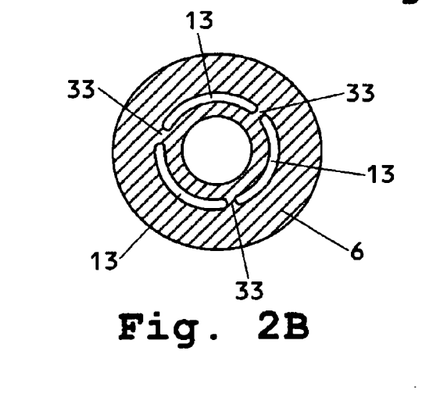
Figure 2C:
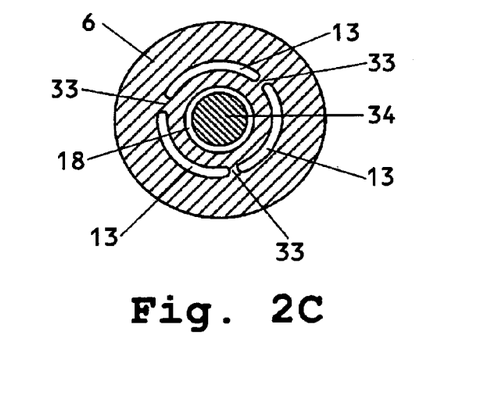

Fluid injection ports 13 are suitably located about the periphery of minor flow outlet 18. Examples of suitable arrangements of the fluid injection ports are illustrated in FIGS. 2A, 2B and 2C for minor flow outlets having a rectangular (FIG. 2A), circular (FIG. 2B) and annular slit (FIG. 2C) cross-section, respectively. In FIG. 2A, minor flow outlet 18 is in the form of a rectangular slit within block 6. Injection ports 13 reside above and below minor flow outlet 18. As shown, optional bridges 33 reside within block 6 between adjacent injection ports 13 to provide structural integrity. In FIG. 2B, minor flow outlet 18 has a circular cross-section within block 6 and injection ports 13 (separated by optional bridges 33) surround the periphery of minor flow outlet 18. In FIG. 2C, minor flow outlet 18 is an annular slit formed by block 6 and central core 34. Injection ports 13 surround minor flow outlet 18 as before.

Fouling of conventional virtual impactor devices is caused by particles colliding with the interior surfaces of the device. In the separation zone, the region in which these collisions are most frequent is that area proximate to the juncture of the major and minor flow outlets, corresponding to reference numerals 11 in FIGS. 3 and 3A. Another region prone to fouling is near the juncture of the inlet to the separation zone and the major flow outlet, corresponding to areas 22 in FIGS. 3 and 3A. The region around juncture 11 tends to foul in conventional devices because some proportion of the particles deviate from the principal direction of flow as the fluid enters the separation zone. The reduced pressure in this zone (due to the suddenly wider cross-section and/or a vacuum in this area) causes most of the fluid to be diverted into the major flow outlet. The fluid flow carries some particles with it into the major flow outlet. However, the particles have greater mass, and therefore greater inertia, and some of them assume a direction of travel that results in impact at or near juncture 11.

The regions at or near junctures 22 tend to foul in prior art devices because of eddies and/or recirculation within the fluid near this region, resulting in deposition of particles on the walls.

The first aspect of this invention alleviates fouling at juncture 11 and surrounding regions, and in the preferred embodiments alleviates fouling at junctures 12.

During operation of the inventive device, a particle-laden fluid enters virtual impactor 1 through inlet 12. In this invention, a "fluid" is considered to be any material capable of fluid flow, including gasses, liquids, molten materials, and the like. The invention is particularly useful for removing particles from gasses, including air, nitrogen, oxygen, argon, helium, hydrogen, hydrocarbons, carbon dioxide, chlorocarbons, fluorocarbons, chlorofluorocarbons, various mixtures of gasses and the like. "Particles", in the context of this invention, include both solid particulate matter, as well as liquids that exist as discrete droplets within the fluid stream. To be separable, the particles need to have mass that is significantly greater than that of the molecules of the carrier fluid. The greater inertia of the particles causes them to change direction more slowly than the molecules of the carrier fluid. Particles having a longest dimension of from about 0.01–100 microns, especially from about 0.1 to about 100 microns, are particularly suitable for removal from a gaseous carrier fluid using this invention. The composition of the particles is generally unimportant to the operation of the invention. The particles may include various types of biological matter such as bacterial spores, viruses, other microorganisms and pollen, and may include pathological agents such as anthrax or smallpox spores. The particles may include other chemical aerosols of all types, including those which have toxological properties. The particles may include inorganic or other organic particulate matter or droplets, such as water droplets, smog particles, smoke particles, dust particles, mineral particles, metal particles, and the like.

As the fluid passes through acceleration nozzle 2,the fluid velocity increases due to the narrowing of channel 17. The geometry of walls 5 of acceleration zone 2 is designed such that the particles of interest become concentrated near the center of the fluid flow exiting acceleration nozzle 2,with peripheral regions of the flow being relatively devoid of such particles. Upon exiting acceleration nozzle 2,the fluid is conducted through inlet 10 to separation zone 3. Separation zone 3 has an area of increased cross-section downstream of inlet 10. This results in a lower pressure area, which causes the fluid to expand outwardly. As the particles have higher mass and therefore higher inertia than the fluid particles, they tend to continue traveling in a relatively straight line, and therefore tend to continue traveling in the principal direction of flow indicated by arrow 14 through minor flow outlet 18. The fluid particles, on the other hand, easily become redirected transverse to the direction of flow of the fluid as it exits the acceleration nozzle. This relative movement becomes the basis for separating a fraction of the flow containing a high particle concentration.

A fluid is injected into separation zone 3 through injection ports 13, as shown more particularly in FIGS. 3 and 3A. Fluid exiting injection ports 13 enters separation zone 3 in a direction approximately opposite to the principal direction of flow indicated by arrow 14. Generally, it is preferred that the fluid injected through ports 13 enters at an angle of no less than 135° to the principal direction of flow. A suitable angle of injection is no less than 160° to the principal direction of flow. It is generally desirable to minimize flow of the injected fluid into the main path of the particles through the separation zone along linear axis 14.

The fluid injected through injection ports 13 forms a fluid barrier to particles that would otherwise impact the interior walls of separation zone 3 near juncture 11. As shown in more detail in FIG. 3A, the fluid exiting injection ports 13 enters separation zone 3 in the general direction indicated by arrows 35. This flow causes the fluid flowing toward junction 11 to become diverted away from juncture 11, in the general directions indicated by arrows 113 and 115. Particles carried by that fluid are similarly re-directed into the directions indicated by arrows 113 and 115, so they pass through minor flow outlet 18 or major flow outlet 9. This effect reduces the frequency of particles coming into contact with the interior walls of separation zone 3 near juncture 11 and thus reduces fouling.

In the preferred embodiment illustrated in FIGS. 3 and 3A, fluid injection ports 25 reside proximate to junctures 22 of inlet 10 into separation zone 3 and major flow outlet 9. The design and operation of fluid injection ports 25 is similar to fluid injection ports 13, as already described. Fluid exiting injection ports 25 enters separation zone 3 in a direction approximately aligned with the principal direction of flow indicated by arrow 14. Generally, it is preferred that the fluid injected through ports 25 enters at an angle of no greater than 45° to the principal direction of flow. A suitable angle of injection is no greater than 20° to the principal direction of flow. As shown in FIG. 3A, fluid injected through injection ports 25 forms a fluid barrier to particles that would otherwise impact the interior walls of separation zone 3 near juncture 22. Fluid exiting injection ports 25 enters separation zone 3 in the general direction indicated by arrows 37. This flow causes the particle-laden fluid flowing toward junction 22 to become diverted away from juncture 22, in the general directions indicated by arrows 116. Particles carried by that fluid are similarly re-directed into the directions indicated by arrows 116, and fouling in the region of juncture 22 is reduced.

The embodiment of the invention illustrated in FIGS. 1 and 4 includes an acceleration nozzle of one aspect of the invention. Turning to FIG. 4, acceleration nozzle 41 includes a concave section shown generally at 42, in which the concavity is defined by the interior dimensions of walls 45 of block 46. Being "concave" here refers to the manner in which the interior width of acceleration nozzle 41 decreases through concave section 42 in the direction of flow. In concave section 42, the angle between the direction of flow and the walls 45 of block 46 continuously increases along the direction of flow. Thus, for example, as shown in FIG. 4, angle $\theta_3<\theta_2<\theta_1$, indicating the concavity of concave section 42 of acceleration zone 41. Further, opposing walls 45 are symmetrical within concave section 42 with respect to a principal axis, which is parallel to the principal direction of flow through concave section 42 and is indicated in FIG. 4 by reference numeral 52.

Acceleration nozzle 41 further includes convex section 43, which is immediately downstream of concave section 42. Being "convex" here refers to the manner in which the interior width of acceleration nozzle 41 decreases through convex section 43 in the direction of flow. In convex section 43, the angle between the direction of flow and walls 45 of block 46 continuously decreases along the direction of flow. As shown in FIG. 4, angle $\theta_6>\theta_5>\theta_4$, indicating the convexity of convex section 42 of acceleration zone 41. Convex section 43 begins at such point where the angle between the direction of flow and walls 45 of block 46 ceases to continuously increase along the direction of flow, and ends at such point that the width of the fluid path through acceleration nozzle 41 reaches a minimum. The region of transition between the concave and convex sections is that at which the angle between the direction of flow and the walls 45 of tube size ceases to decrease and begins to increase. This region is sometimes referred to herein as an "inflection point" and is indicated by reference numeral 55 in FIG. 4. As before, opposing walls 45 are symmetrical within convex section 43 with respect to principal axis 52.

At the inflection point, walls 45 preferably form an angle (indicated as φ in FIG. 1) of from 25–65° to the principal direction of flow. This angle is preferably about 35–55° and especially from about 40–50°.

Convex section 43 includes a fluid outlet through which the particle-laden fluid exits the acceleration zone. In the embodiment shown in FIG. 4, fluid outlet 50 is in fluid communication with a separation zone (not shown). Outlet 50 of convex section 43 is defined herein as the point at which the width of the fluid channel ceases to decrease, i.e., the width either becomes constant or increases in the principle direction of flow.

Figure 4:
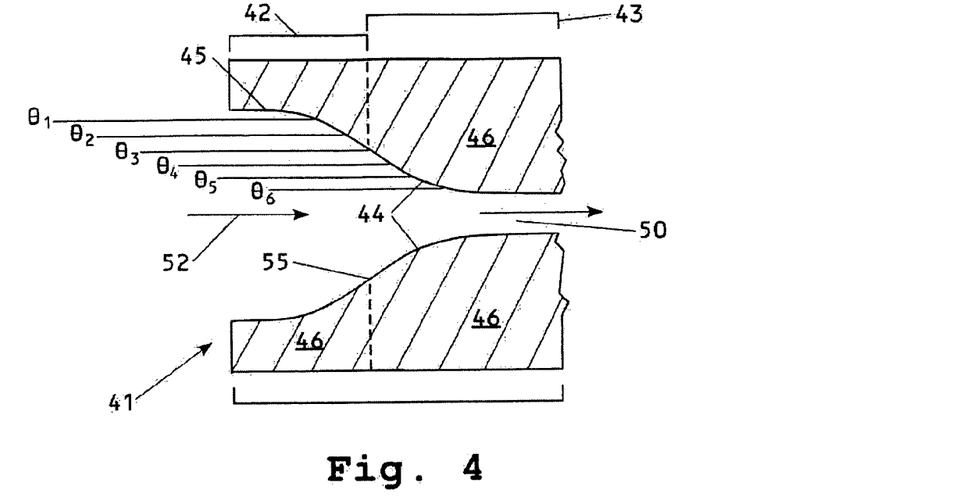
FIG. 4 is an enlarged side view, in section, of an acceleration nozzle of an aspect of the invention.

At any point along wall 45 of block 46 within concave section 42, the curvature of wall 45 can be described in terms of a radius of curvature $R_v$. $R_v$ may be constant or vary throughout the length of concave section. Similarly, a radius of curvature $R_x$ describes the curvature of wall 45 at any point in convex section 43. $R_x$ may vary or be constant along the length of convex section 43. $R_x$ preferably varies, having a minimum (i.e., region of greatest curvature, $R_{xmin}$) proximate to the outlet from convex section 43. In FIG. 4, the point at which $R_{xmin}$ occurs is indicated at reference numeral 44.

In the embodiment shown in FIG. 4, convex section 43 has a relatively large $R_{xmin}$, indicating a rather gradual reduction in width through the section. It is generally preferably that $R_{xmin}$ be much smaller than $R_{vmin}$. $R_{xmin}$ may be as little as zero, i.e., convex section 43 may form a sharp angle rather than a curve at the point of greatest curvature.

A particle-laden fluid entering the acceleration nozzle will typically contain particles that are randomly distributed within the fluid. As the fluid moves through concave section 42, conditions are preferably such that the particles travel in essentially the same direction as the immediately surrounding fluid, with minimal crossing of streamlines. The fluid velocity increases as the fluid traverses concave section 42, due to the continually narrowing width of this section of the acceleration nozzle.

The tendency for a particle to cross streamlines due to a change in direction of a fluid flow can be represented by a Stokes number (STK), which is a ratio of a particle response time scale to the characteristic flow time scale. The Stokes number can be related to particle, fluid and flow characteristics by the relationship (I)

$$STK = \frac{\rho_p U d_p^2}{18\mu D} \quad (I)$$

where $p_d$ represents the density of the particle, U represents the local flow velocity in the principle direction of flow, $d_p$ represents the particle diameter, μ represents the viscosity of the fluid, and D represents the local width or diameter of the conduit. Higher Stokes number values indicate a greater tendency for particles to experience turbulent flow, crossing streamlines within the flow and in effect move in a direction other than that of the immediately surrounding fluid. In concave section 42 of acceleration nozzle 41, it is preferred to maintain conditions such that the flow is characterized by a Stokes number (STK) that is less than 0.5 and preferably less than 0.25, such as from about 0.05 to about 0.25, from about 0.05 to about 0.15, or from about 0.05 to about 0.1, for the largest particles that are to be concentrated and collected. Under these conditions of flow, even the largest particles will tend to move with the surrounding fluid, with minimal crossing of streamlines. Movement of the smaller particles within the fluid will be characterized by a smaller Stokes number and will have an even greater tendency to move with the surrounding fluid, as desired.

In convex section 43, fluid (and particle) velocity continues to increase, and conditions are selected such that the particles develop sufficient inertia to cross streamlines and become concentrated towards the center of the flow. As a result, the fluid exiting convex section 43 through outlet 50 will typically have a gradient of particle concentration. The fluid near the center of the flow exiting convex section 43 will tend to have a relatively high concentration of particles, whereas the fluid near the periphery of the flow (i.e. closer to walls 45 of block 46 in the embodiment shown in FIG. 1) will tend to have a lower concentration of particles. Outermost regions of the fluid exiting convex section 43 may be substantially devoid of particles. Particle concentration will tend to increase gradually from the outside toward the center of the fluid exiting convex section 43.

Flow conditions that favor the movement of particles across streamlines are generally characterized by a Stokes number value of at least 1.0. The Stokes number can alternatively be expressed in terms of the change in flow velocity between adjacent streamlines according to equation (II)

$$STK = \frac{\partial u / \partial s}{18 \mu / \rho_d d_p^2} \tag{II}$$

where ∂u/∂s represents the change in velocity across a streamline, and $d_p$, μ and $p_d$ are as previously defined. In convex section 42, the diameter of the smallest particles to be concentrated and separated are of interest, as they have the smallest inertia and are most resistant to slipping across streamlines and becoming concentrated in the center of the flow, as desired. Larger particles will be associated with Stokes number values greater than those of smaller particles, so if the Stokes number value of the smallest is greater than 1.0, as desired, the Stokes number values of larger particles will meet that criterion as well.

Operating conditions needed to obtain the desired concentration of particles near the center of the flow exiting the acceleration nozzle will depend on several factors. These include the geometry of the nozzle, the velocity of the fluid as it enters the nozzle, the velocity of the fluid as it exits the nozzle, the viscosity of the fluid, the size of the particles and the particle density. Not all of these factors are independent. For example, entrance and exit velocities will usually be related by some factor that depends on the particular geometry of the nozzle. Thus, for a particular nozzle design and entrance velocity, the exit velocity is generally fixed, for any given fluid.

The value of ∂u/∂s can be estimated using the relationship $$\partial u/\partial s \approx Q(U/R) \tag{III}$$

where Q represents the flow rate (volume/unit time), U represents the average local flow velocity in the principal direction of flow and R represents the local radius of curvature of the streamline. As the value of R is determined mainly by the local radius of curvature of walls 45 of block 46, R is taken to be equal thereto. This allows one to relate the Stokes number characteristic of the flow at a given point within the acceleration nozzle to the local radius of curvature of walls 45 as follows:

$$STK \approx \frac{Q(U/R)}{18\mu/\rho_d d_p^2} \quad \text{(IV)}$$

In concave section 42 of acceleration nozzle 41, conditions resulting in the highest characteristic Stokes number will exist at the point of smallest radius of curvature $R_{vmin}$. Flow conditions are therefore established such that the Stokes number value in the region of smallest radius of curvature in concave section 42 fall within the ranges listed above, for even the largest particles to be concentrated and collected. Similarly, in convex section 43 of acceleration nozzle 41, conditions resulting in the highest characteristic Stokes number will exist at the point of smallest radius of curvature $R_{xmin}$. In at least one region of convex section 43 of acceleration nozzle 41, the radius of curvature of walls 45 is sufficiently small that flow conditions represented by a Stokes number of at least 1.0 are created for the smallest particles that are desirably concentrated and collected.

For concentration and separation of particles in the 1–10 micron size range, the following conditions are generally suitable:

Inlet width or diameter (at point of entry into nozzle): 1–20 mm, especially 2–10 mm and preferably 3–7 mm.
Outlet width or diameter: 0.25–5 mm, especially 0.25–2 mm, preferably 0.4–1.0 mm.
Ratio, inlet to outlet width or diameter: 3–50, especially 4–30, preferably 4–10.
Ratio. $R_{vmin}/R_{xmin}$: >10, especially 15–100, preferably 20–50.
$R_{xmin}$: 0 to 3 mm, especially 0 to 1.5 mm and preferably 0.2 to 0.75 mm.
Flow velocity: $\geq$100 m/s.

A preferred acceleration nozzle has an inlet width or diameter of 2–10 mm, an outlet width or diameter of 0.25–2 mm, a ratio of inlet/out width or diameter of 4–10, an $R_{xmin}$ of 0–1.5 mm and a ratio, $R_{vin}/R_{xmin}$, of at least 10. A more preferred acceleration nozzle has an inlet width or diameter of 3–7 mm, an outlet width or diameter of 0.4–1.0 mm, a ratio of inlet/out width or diameter of 4–10, an $R_{xmin}$ of 0–1.5 mm and a $R_{vmin}/R_{xmin}$ ratio of 15–100. An even more preferred acceleration nozzle has an inlet width or diameter of 3–7 mm, an outlet width or diameter of 0.4–1 mm, a ratio of inlet/out width or diameter of 4–8, an $R_{xmin}$ of 0.2–0.75 mm and a ratio, $R_{vin}/R_{xmin}$ of 20–10.

The acceleration nozzle may be circular, may be an elongated or annular slit, or may have some other cross-sectional shape, transverse to the principle direction of flow of the fluid through the nozzle, provided that the width or diameter of the nozzle decreases through concave and convex sections as described before.

The design of the acceleration nozzle of the invention helps provide for efficient particle concentration and collection. Fouling due to particle collection on the interior walls of the impactor is reduced due to the geometry of the impactor, when flow conditions are selected properly. Fouling within the acceleration nozzle itself is believed to be reduced by reducing areas of eddy currents, i.e.,recirculation of the fluid, within the nozzle. In addition, the improved focusing of the particles near the center of the outlet stream tends to reduce fouling in downstream separation zones, such as zone 13 of FIG. 1. As a result of these operational benefits, the virtual impactor of the invention tends to operate more efficiently, with reduced fouling. The reduction in fouling reduces maintenance costs, prolongs the life of the impactor device and allows for a greater proportion of particles to be captured (which can be especially important when the particle concentration is low).

The performance of the acceleration nozzle can be expressed as a comparison of the particle concentration in the minor flow exiting the separation zone with the particle concentration of the starting fluid. The acceleration nozzle of the invention often concentrates the particles by a factor of from about 3 to about 30 or more. For many applications, it is preferred to select operating conditions, such as flow rates, in conjunction with acceleration nozzle geometry, choice of fluid and particle size of interest, to obtain a concentration factor of at least 10, preferably at least 15.

Figure 5:
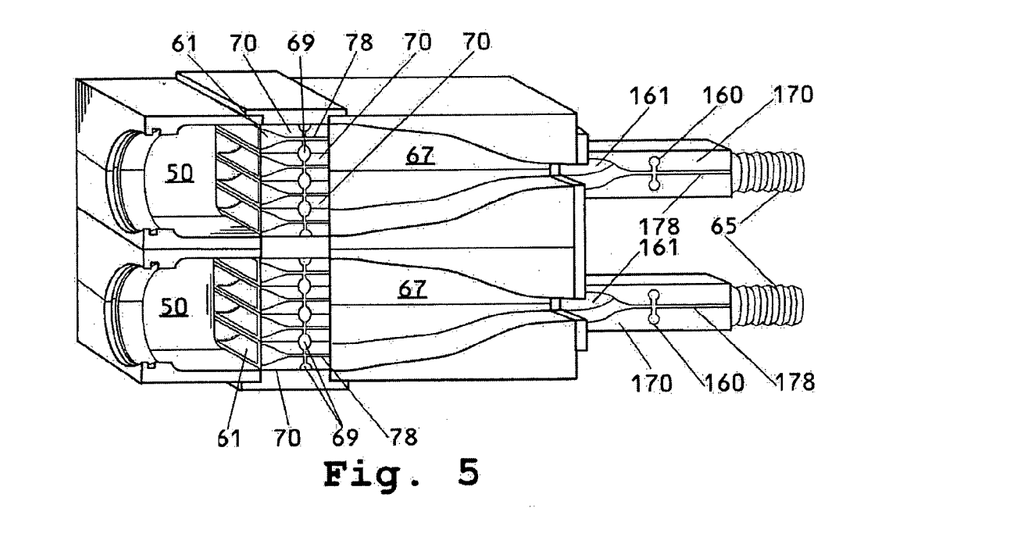
FIG. 5 is an isometric view, in section, of a two-stage virtual impactor device of the invention.

If it is desired to further concentrate the particles, the stream exiting through the minor flow outlet can be directed into one or more additional concentrating devices, including one or more downstream virtual impactor devices, particularly one or more downstream virtual impactor devices according to the invention. These are desirably arranged in sequence, with the output from each device forming the feed for the next device that is immediately downstream. The virtual impactor of the invention can be combined with one or more concentration devices of like or different types in a single housing to form an integrated device. Such an arrangement is illustrated in FIG. 5. It is also possible to subject the fluid exiting major flow outlet 9 (FIG. 1) to subsequent particle concentration and collection steps to remove any residual particles that are not cleanly separated. This is of particular interest when the virtual impactor device of the invention is used in air or gas purification applications, where it is desired to produce a gas stream that is purified as much as possible.

The particles contained in the particle-laden stream exiting through minor flow outlet 18 (FIG. 1) can be captured if desired using a variety of particle capturing techniques and apparatus. In certain preferred embodiments of the invention, therefore, the virtual impactor device is in fluid communication with at least one particle collection means which removes the particles from the concentrated stream and collects them on a substrate or in some suitable holder or container. It is especially preferred that the particle collection means is contained in a common housing with the virtual impactor of the invention to form an integrated device.

A variety of mechanical filters can be used to capture the particles and separate them from the remaining volume of fluid. Suitable particle collection means include HEPA filters, nanofilters, slides for use in various analytical devices, filter bags, and the like.

Of particular note are so-called micropillar type impactor devices, such as are described in U.S. Pat. No. 6,110,247 and copending patent application Ser. Nos. 10/805,869, 10/805,791 and 60/555,159, all filed Mar. 22, 2004. Such microimpactor devices include multiple rows of small scale pillars that are separated from each other slightly to define fluid channels between adjacent microimpactor within a row and between adjacent rows of microimpactors. The microimpactor device also takes advantage of the greater inertia of the particulate matter, which cannot change direction with the fluid as it passes through the microimpactor array, and therefore contacts and becomes adhered to the microimpactor surfaces. The microimpactor devices have the advantage of operating at low pressure drops and of being capable of being tailored to capture specific size particles, or even particles having specific affinities for the microimpactor surface.

In many applications, the particle collector will function simply as a physical barrier to the movement of the particles, and as such the particular material of construction may not be especially important. However, there are many applications in which it is desirable that the surface of the particle collector interact with the particles in some manner beyond presenting a simply physical barrier. In those instances, the collector surface is desirably prepared from a substance that will interact with the particles in the desired manner. To this end, the surface of the particle collector may be treated or coated in various ways to promote the desired type of interaction with the particle.

Examples of interactions of this type include enhanced adhesion, decreased adhesion (for example, to facilitate cleaning), electrostatic attraction and/or repulsion, adsorption, deactivation, oxidation and/or reduction, lysing, catalysis, identification reactions, polymerization, other chemical reactions, analysis, and the like.

For example, the particle collector may be coated with an adhesive so that the particles adhere better to the collector and are more efficiently removed from the fluid stream. A wide range of adhesives is suitable. A particularly suitable type of adhesive is one that will release the particles when desired, such as by wetting, so the particles can be recovered and/or the collector cleaned. A particular adhesive that loses tack when wet is available from the Washington Technology Center, Seattle, Wash., under the trade name Tetraglyme™.

Alternatively, the particle collector surface may be made from or coated with a non-stick material, such as a fluorinated polymer like Teflon™ fluoropolymer or Paralene™ polymer material (available from EM Corporation, Peachtree, Ga.) to enhance removal and/or recovery of the particles.

The particle collector can be charged in order to electrostatically attract and bind the particles, and/or to deactivate or decompose the particles. In such a case, the collector is advantageously made of, doped with or coated with a conductive or semiconductive material, which is in electrical connection to an electrical power source that supplies the necessary charge. An electrostatic attraction to the particles can be increased by applying an electrostatic charge to the particles themselves, at some point prior to passing the particle-laden stream through the microimpactor array. In one such embodiment, the particle-laden fluid is caused to flow through such a spray zone, and then into the collector, which is directly or indirectly in fluid communication with the spray zone. The spray zone includes a conduit for the particle-rich fluid exiting the acceleration nozzle of the invention, and an apparatus for forming electrostatically charged droplets and spraying them into the fluid stream where they contact the particles. Atomizers of various types are known and are suitable. Examples of such sprayers include those described in U.S. Pat. Nos. 4,255,777, 4,439, 980, 4,784,323, 5,062,573, 5,378,957, 6,227,465, 6,318,648 and WO 01/21319A1, all incorporated herein by reference. A particular preferred type of atomizer is described in U.S. Pat. No. 6,820,456, incorporated herein by reference. That atomizer includes (A) at least one microinjector including (1) an orifice through which the liquid is brought in contact with a pin emitter and (2) a conductive pin emitter extending outwardly from said orifice, the pin emitter having a radius of curvature in at least one location external to said orifice of no greater than 500 μm; B) means for introducing the liquid to be atomized through the orifice and to the pin emitter, and C) means for connecting said pin emitter to a voltage source. The liquid is preferably under a hydrodynamic pressure of 5 inches of $H_2O$ or less.

Other materials of construction or coatings for the particle collector surfaces include various types of materials that decompose and/or deactivate the particles, catalyze their decomposition and/or deactivation, catalyze some other reaction of the particles with themselves or other materials (including the microimpactors themselves), or else react directly with the particles. A wide range of such materials is possible, depending on the specific application. Deactivation and/or decomposition are particularly desirable in the case where the particles are pathogenic and/or toxic. In that case, the particle collector surface can include, for example, a strong oxidant or reducing agent, or a toxin for the particles (in the case of a biological material). An example of such a deactivating agent is a platinum-on-alumina catalyst, which has been developed as an air purification catalyst for use against nerve agents. If the fluid sample is thought to contain multiple types of pathogenic and/or toxic agents, different portions of the collector can be treated with different coatings, or made of different materials, each of which will deactivate and/or decompose a specific type of suspected pathogenic or toxic agent. Alternatively, multiple collectors have different surface compositions can be used to the same effect.

Yet other materials of construction or coatings for the particle collector surface include antibodies, ligands and membrane materials, which can perform, for example, enhanced particle capture, identification, inactivation, catalytic and/or reagent functions.

The particle collector may be made of or include a piezoelectric material, if desired, so that controlled movement and/or physical distortion of the collector can be caused through the application of an electrical current. This is particularly applicable when a microimpactor type particle collector is used.

The particle collector may be connected to electrical circuitry through various types of edge connector devices. Electrical circuitry includes, for example, connections to sources of electrical power and various kinds of detection and/or analytical devices.

Captured particles and absorbed may be removed from the particle collector using various methods, such as the application of heat (to degrade, volatilize or combust the particles), by backwashing with a fluid flow in the reverse direction, flushing with solvents, removal or reversal of an applied electrostatic charge, various mechanical methods such as brushing, wiping, washing and the like, as well as other methods. Removed particles can be disposed of, taken for analysis, or used for various purposes as desired. If desired, the entire collector can be removed and subjected to analysis, deactivation or recovery of the captured particles.

The acceleration nozzle of the invention can be used as a stand-alone device or combined with various other components to form an assembly that is adapted for specific applications. Examples of specific applications and devices that incorporate a particle collector are described below.

A. Simple particle filtration. In these applications, the device operates simply to capture particles to remove them from a particle-laden fluid, primarily for cleaning purposes. The device includes at least the acceleration nozzle of the invention and at least one particle collector. The captured particles may be removed from the device if desired, so that the device can be re-used. Alternatively, the used device (or simply the particle collector) may be disposed of along with the captured particles and replaced as needed. Particle filtration devices of this type can include, for example, means as described before, in fluid communication with the acceleration nozzle, for creating a flow of the fluid through the device; means for applying an electrostatic charge to the particle collector or some portion thereof; means for applying an electrostatic charge to the particles; an optional prefilter or postfilter in fluid communication with the device for removing larger or smaller particles that are not captured by the device, an optional means to pre-sort incoming particles by size or to remove the bulk of the particles; a fluid inlet and fluid outlet to the device, and optionally means for accessing the particle collector for replacement, maintenance and/or cleaning. Such accessing means include, for example, various types of openings, which may be reclosable, through which the collector can be removed from the device and/or manipulated, cleaned or repaired.

Similarly, the integrated acceleration nozzle and particle collector of the invention can used as a pre- and/or postfilter an apparatus or system that includes at least one other filtration device, such as a screen, a virtual impactor, or an inertial separator. In pre-filtration applications, the device of the invention can remove particles of a pre-determined size that may be too small or two large to be captured efficiently by the main filtration apparatus. A device in which the device of the invention functions as a pre- or postfilter includes, in fluid communication, a fluid inlet, a main filtration device, a fluid outlet, at least one acceleration nozzle/collector device of the invention located upstream (in the case of a prefilter) and/or downstream (in the case of a postfilter) of the main filtration device and optionally at least one means for creating a flow of the fluid through the apparatus. The apparatus may contain means to electrostatically charge the particle collector and/or the particles.

In post-filtration applications, the acceleration nozzle/particle collector of the invention can be used to capture particles that are not collected by the main filtration device, or as a sensor or a component of a sensor that indicates the condition and/or remaining useful life of the main filter. As the main filter ages or becomes laden with captured particles, its openings can become almost entirely blocked. This causes the pressure drop across the filter to increase and the volume of particles passing through the filter to decrease. Conversely, aging or dirty filters often develop defects that allow particulate matter to pass through that would otherwise be captured. The rate at which particles are captured by the post-filter is therefore indicative of the condition of the main filter. This rate may be determined visually by simply inspecting the post-filter system, by removing the post-filter system for remote analysis, or by conducting an in situ analysis of collected particles.

B. Particle recovery. Captured particles can be recovered for analysis or use using a variety of particle recovery techniques such as described above. Devices adapted for such applications are typically similar in design to those used for filtration applications, and include in fluid communication, a fluid inlet, the acceleration nozzle of the invention, at least one particle collector and optionally at least one means for creating a flow of the fluid through the device. The device may contain means for electrostatically charging the particles and/or the particle collector. Devices for particle recovery applications preferably include means for accessing the collector for analysis, replacement, maintenance and/or cleaning, as described before.

C. Particle classification. In these applications, the acceleration nozzle of the invention forms part of an apparatus that sorts particles by, for example, size, weight, shape, composition or other characteristics. In a simple application, the apparatus classifies particles on the basis of mass, by means of a separation zone as described before, downstream of the acceleration nozzle, designed such that large particles exit with the minor fluid flow and the smaller particles exit with the major fluid flow.

However, the apparatus is not so limited, and can be designed to separate particles on the basis of a variety of predetermined characteristics. For example, the apparatus may contain a particle collector that selectively removes particles having a predetermined characteristic, such as size, composition, surface characteristics, electrostatic charge, and the like, while allowing particles lacking that characteristic to pass. Similarly, multiple collectors can be used in series or parallel to classify and capture particles having different characteristics. In such cases, two or more of the collectors will differ from each other in some manner that allows each of them to selectively remove particles having different characteristics from the fluid stream. For example, a particle classification device may contain a first collector that captures particles of a first size range, and a second collector that captures particles of a smaller or larger size range. The two collectors are preferably arranged in series and in fluid communication with each other, with the device having a fluid outlet downstream of the collectors and a fluid inlet to the acceleration nozzle. The collectors are in fluid communication with the outlet of the acceleration nozzle. It is preferred to interpose a separation zone between the acceleration nozzle and collectors to remove a portion of the fluid so that a concentrated stream is fed to the collectors.

Alternatively, a particle classification device may contain a first collector that is electrostatically charged, and thus captures electrostatically charged particles. The device will include means for applying an electrostatic charge to the collector. Such a device optionally includes means for introducing an electrostatic charge onto the particles, preferably located upstream of the charged collector. Suitable devices for introducing an electrostatic charge are described in various references mentioned above. As before, the collectors are in fluid communication with the outlet of the acceleration nozzle, and it is preferred to interpose a separation zone between the acceleration nozzle and collectors to remove a portion of the fluid so that a concentrated stream is fed to the collectors.

A particle classification device can alternately include a first collector that has surface characteristics that enable it to preferentially capture particles that chemically interact with the collector surface. A second collector is then provided to capture other particles that are not collected by the first collector.

In all cases where the device contains two or more particle collectors, the various collectors may all be of the same general type, or if desired two or more different types of collectors can be used. For example, a microimpactor system as described above may be used as one of the collectors, and one or more of the other collectors may be of a different type, such as a HEPA filter, nanofilter, analytical slide, filter bags, and the like. Alternatively, the particle collectors may all be of the same general type, differing from each other by some characteristic that allows the separate particle collectors to capture particles that are distinguishable from each other in some predetermined way. An especially preferred device includes two or more microimpactor systems, where the microimpactors of the individual systems differ from each other in the geometrical arrangement of the microimpactors, materials of construction and/or surface characteristics in such a way that the separate microimpactor systems each preferentially capture a distinct subset of the particles.

D. Particle Analysis and/or Detection. In these applications, particles separated from the main fluid flow are subjected to one or more analytical techniques to determine physical, chemical and/or biological attributes, or to indicate the presence of certain types of particles. Particle analysis or detection can be performed by capturing the particles and performing analytical and/or detection steps upon them after removing the collected particles from the collector, or while they remain on the particle-laden collector. In the latter case, particle analysis or detection can be done performed in-line and continuously, if desired.

The particular analytical or detection technique to be used will of course depend on the particles and the nature of the evaluation. Collected particles may be removed from the microimpactor system if desired or necessary using techniques as set forth above.

For in-line particle analysis and detection, the collected particles may be interrogated using a variety of sensing techniques, including visible and/or UV fluorescence, tetrahertz spectroscopy, Raman spectroscopy, IR spectroscopy, mass spectroscopy, MALDI-MS and the like. In these applications, it is preferred that the collector is transparent to the particular sensing device, or else distinguishable from the captured particles by that particular sensing device. The collector may instead be made from or coated with various types of reagents, probes or biological materials such as ligands or antibodies, which engage in a chemical reaction or bond to specific types of particles and thereby indicate the presence of those particles in the fluid.

Thus, a particle analyzer according to an aspect of the invention includes one or more acceleration nozzles of the invention, a fluid inlet and fluid outlet to the device in fluid communication with a collector, and at least one analytical device adapted to interrogate the collector for detection and/or analysis of captured particles. Such a particle analyzer may contain various optional but preferred features as have been described before with respect to other applications, including, for example, circuitry for powering and operating the analytical device and for obtaining data from the analytical device and converting it to human-readable form; various types of readouts and displays; means for creating a flow of the fluid through the device; an optional prefilter or postfilter in fluid communication with the device for removing larger or smaller particles that are not captured by the device, an optional means to pre-sort incoming particles by size or to remove the bulk of the particles; and optionally means for accessing the collector for replacement, maintenance and/or cleaning. If desired, the entire particle analyzer can be mounted onto an integrated circuit board or other device, in order to integrate particle collection and detection/analysis. The analytical device can be of various types as described in the preceding paragraph.

A particle detection device according to an aspect of the invention is of similar design, except that instead of or in addition to the analytical device, reagents, probes or biological materials such as ligands or antibodies are present on the surface of the collector to indicate the presence of specific types of particles in the fluid.

In another type of detector device, the collector is made from an optically transparent material such as quartz that is coated with a nuclear detection material (such as copper or nanoporous copper) that generates photons when it detects a particular material of interest. The collector is connected to a fiber optic material that transmits the generated photon to a collector. The circuitry may include a filter, that allows only photons of a desired wavelength to pass (to remove noise or signals from species that are not of interest) and a photomultiplier to increase the signal.

E. Particle lysing, deactivation, catalysis and chemical reactions. Particles captured by the device of the invention can be subjected to a wide variety of operations, examples of which are lysing, deactivation, catalysis, and various chemical reactions such as oxidation or polymerization. This can be accomplished in several ways. Captured particles may of course be recovered from the collector and treated. The collector itself may be made from, be coated with or otherwise contain an agent that reacts with the captured particle to accomplish the desired operation. Alternatively, the particle-laden collector may be exposed to an agent which accomplishes that operation. The collector may also conduct electrical or thermal energy to the captured particles for performing lysing, other electrochemical reactions or thermal degradation of captured particles.

A specific example of the foregoing is the deactivation of toxic chemical and biological agents and pathogens. In many military and civilian applications, it is necessary to protect individuals from ambient air-borne toxic materials and pathogens. Such toxic materials may include nerve agents, perfluorocarbons, other gaseous toxins, pathogenic microorganisms such as anthrax, smallpox or viruses, and the like. In such applications, a personal protection apparatus such as a breathing apparatus includes a device including the acceleration nozzle of the invention and a particle collector, in which the particle collector made from or coated with materials that react with, bind or otherwise deactivate specific types of air-borne toxins and pathogens. Thus, the device serves not only to capture toxic and pathogenic particles, but also to render them into a non-hazardous or less hazardous form. A wide variety of deactivating materials can be used to make or coat the particle collector, as described above. Combinations of different deactivating materials can be used to provide protection from mixtures of toxic agents and/or pathogens. For example, a portion of the collector may be coated with a deactivating agent for one specific toxin or pathogen, whereas other portions are coated with a different deactivating agent for some other toxin or pathogen. Separate, differently coated collectors can also be used.

Alternatively or in addition, the particle collectors may be connected with a source of electrical energy, which allows the collectors to become electrostatically charged and lyse or inactive the toxic or pathogenic agent. The collectors may be combined with an energy source that heats the collectors and thermally lyses or inactives the toxin or pathogen.

In another alternative, the particle collector surface is made from or is coated with a catalyst that catalyzes a lysing or deactivation reaction between a toxin or pathogenic agent and some other reagent. The other reagent can be supplied together with or separately from the particle-laden fluid to perform the lysing or deactivation reaction on the captured particles.

A breathing device containing a device as described can replace or supplement conventional gas mask technology. It is also scalable to collective protection applications such as shelters.

EXAMPLE

A two-stage virtual impactor device is constructed as shown in FIG. 5. In the first stage, eight virtual impactor devices 70 are arranged vertically, in two groups of four. Each group of four first-stage virtual impactors are connected to a common inlet duct 50 and a common outlet duct 67. Each virtual impactor device 70 includes an acceleration nozzle 61, a major flow outlet 69 and a minor flow outlet 78.

The second stage includes two vertically arranged virtual impactor devices 170 which include acceleration nozzles 161, major fluid outlets 160 and minor flow outlets 178. Each of the two second stage impactor devices accepts a stream from one set of four first stage virtual impactor devices. Fluid exiting through minor flow outlets 178 is separately withdrawn through ducts 65.

Figure 6A:
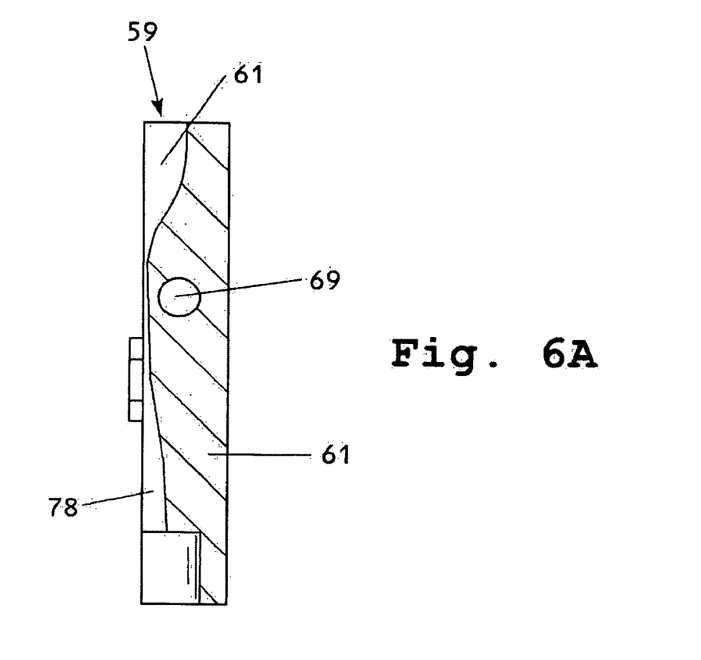
FIGS. 6A and 6B are side and isometric views, respectively, of a block that constitutes a half of a virtual impactor device according to one aspect of the invention.
Figure 6B:
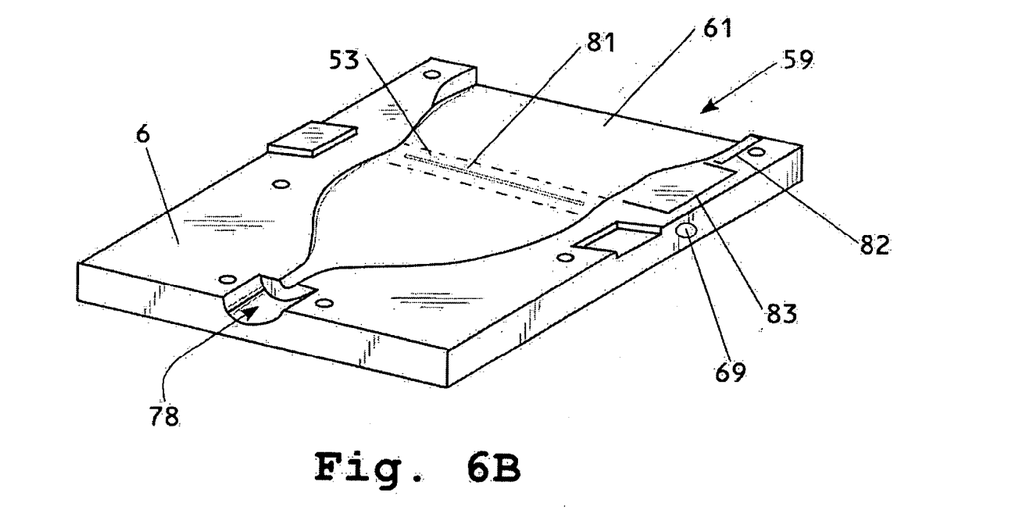

All of the virtual impactor devices 70 and 170 are of the same design. All are made by machining identical top and bottom halves from an aluminum block. The blocks are illustrated in FIGS. 6A and 6B. In FIGS. 6A and 6B, block 6 includes acceleration nozzle 61 in fluid communication with separation zone 53. Acceleration nozzle 61 includes a concave section 82 followed by convex section 83, in accordance with the invention. Separation zone 53 includes rectangular slit 81, which is in fluid communication with major flow outlet 69. Block 6 also includes minor flow outlet.

Blocks 6 are 2.5 inches long, 2 inches wide and 0.375 inches thick. Rectangular slit 81 is 1.19 inches across and 0.05 inches wide. The distance from fluid inlet 59 to rectangular slit 81 is 0.863 inches. Rectangular slit 81 is located at the center of a region of constant cross-section that is 0.25 inches in length and begins 0.75 inches downstream of fluid inlet 59. Concave section 82 of acceleration nozzle 61 has an $R_{vmax}$ of 0.700 inches. Similarly, convex section 83 of acceleration nozzle 61 has an $R_{xmax}$ of 0.700 inches. Fluid inlet 59 to acceleration nozzle 61 (after the blocks are assembled) has dimensions of 1.31 by 0.30 inches. The outlet from acceleration nozzle 61 to separation zone 53 is about 0.01 inches wide. Minor flow outlet 78 has a radius of about 0.909 inches. Major flow outlet 69 has a radius of about 0.18 inches.

The two-stage apparatus is evaluated by injecting an air stream containing 1 micron Fluoresbrite YB Microspheres (from Polysciences Inc.) at a concentration of approximately 1000 particles per liter. Flow rate into the apparatus is 15 liters/minute. Four duplicate runs of 30 seconds each are made. The concentration of particles exiting the apparatus through duct 65 is measured using an APL Isokinetic sampling manifold. Under these conditions, the particle concentration in the gas exiting through duct 65 is about 4130 particles/liter (average of the four runs), resulting in a concentration factor of ~4.13.

When this experiment is repeated using 2 micron Fluoresbrite YB Microspheres, the concentration factor is approximately 18.9. This indicates that flow rates and conditions are better optimized in these experiments for concentrating the larger particles.

What is claimed is:

1. A virtual impactor device comprising an acceleration nozzle and a separation zone both aligned about a linear axis which defines a principal direction of aerosol flow through the device from the acceleration nozzle through the separation zone, the acceleration nozzle having a fluid inlet and a substantially narrower fluid outlet, and the separation zone includes an inlet from the acceleration nozzle, a minor flow outlet downstream from the acceleration nozzle and oriented substantially along the linear axis; and at least one major flow outlet downstream from the acceleration nozzle and oriented at an angle to the linear axis, the minor flow outlet and the major flow outlet meeting at a juncture, and a fluid injection port proximate to the juncture of the major flow outlet and the minor flow outlet adapted to inject a fluid into the separation zone.

2. The virtual impactor device of claim 1, further comprising at least one means of analyzing a physical, chemical and or biological attribute of particles exiting the minor flow outlet.

3. The virtual impactor device of claim 1, wherein the inlet from the acceleration nozzle and the major flow outlet meet at an upstream juncture, and the device further comprises a second injection port proximate to the upstream juncture, said second injection port being adapted to inject a fluid into the separation zone in approximately the principal direction of aerosol flow through the impactor device.

4. The virtual impactor device of claim 1, wherein
   a) the acceleration nozzle comprises a conduit which narrows in a principal direction of flow from a fluid inlet into the aerosol concentration device towards the separation zone,
   b) the acceleration nozzle includes a concave section in which the interior width of the acceleration nozzle decreases in the principal direction of flow; and
   c) the acceleration nozzle includes a convex section downstream of the concave section, wherein the interior width of the acceleration nozzle further decreases in the principal direction of flow and through which the aerosol is directed through a nozzle outlet.

5. The virtual impactor device of 1, further comprising at least one particle collection means in fluid communication with the minor flow outlet.

6. The virtual impactor device of claim 4, further comprising at least one particle collection means in fluid communication with the minor flow outlet.

7. The virtual impactor device of claim 5, further comprising an apparatus for applying an electrostatical charge droplets onto particles exiting the minor flow outlet.

8. The virtual impactor device of claim 7, further comprising an apparatus for forming electrostatically charged droplets and spraying the droplets onto particles exiting the minor flow outlet.

9. The virtual impactor device of claim 6, further comprising an apparatus for applying an electrostatical charge droplets onto particles exiting the minor flow outlet.

10. The virtual impactor device of claim 9, further comprising an apparatus for forming electrostatically charged droplets and spraying the droplets onto particles exiting the minor flow outlet.

11. A method for forming a fluid having an increased concentration of particles, comprising
   a) flowing a particle-laden fluid through a virtual impactor device, wherein the virtual impactor device includes an acceleration nozzle and a separation zone both aligned about a linear axis which defines a principal direction of aerosol flow through the device from the acceleration nozzle through the separation zone, acceleration nozzle having a fluid inlet and a substantially narrower fluid outlet, and the separation zone includes an inlet from the acceleration nozzle, a minor flow outlet downstream from the acceleration nozzle and oriented substantially along the linear axis; and at least one major flow outlet downstream from the acceleration nozzle and oriented at an angle to the linear axis, the minor flow outlet and the major flow outlet meeting at a juncture, and a fluid injection port proximate to the juncture of the major flow outlet and the minor flow outlet adapted to inject a fluid into the separation zone;
   b) injecting a fluid into the separation zone through the fluid injection port;
   c) withdrawing a major flow depleted in the particles through the major flow outlet; and c) withdrawing a minor flow having an increased concentration in particles through the minor flow outlet.

12. The method of claim 11, wherein the inlet from the acceleration nozzle and the major flow outlet meet at an upstream juncture, the device further comprises a second injection port proximate to the upstream juncture, said second injection port being adapted to inject a fluid into the separation zone in approximately the principal direction of aerosol flow through the impactor device, and fluid is injected through said second injection port into the separation zone.

13. The method of claim 11, wherein
a) the acceleration nozzle comprises a conduit which narrows in a principal direction of flow from a fluid inlet into the aerosol concentration device towards the separation zone,
b) the acceleration nozzle includes a concave section in which the interior width of the acceleration nozzle decreases in the principal direction of flow; and
c) the acceleration nozzle includes a convex section downstream of the concave section, wherein the interior width of the acceleration nozzle further decreases in the principal direction of flow and through which the aerosol is directed through a nozzle outlet.

14. The method of claim 11, further comprising collecting particles exiting the minor flow outlet.

15. The method of claim 11, further comprising forming electrostatically charged droplets and spraying the droplets onto particles exiting the minor flow outlet.

16. The method of claim 11, further analyzing at least one physical, chemical and or biological attribute of particles exiting the minor flow outlet.

17. An aerosol concentration device comprising an acceleration nozzle wherein
a) the acceleration nozzle comprises a conduit which narrows in a principal direction of flow from a fluid inlet into the aerosol concentration device towards the separation zone,
b) the acceleration nozzle includes a concave section in which the interior width of the acceleration nozzle decreases in the principal direction of flow; and
c) the acceleration nozzle includes a convex section downstream of the concave section, wherein the interior width of the acceleration nozzle further decreases in the principal direction of flow and through which the aerosol is directed through a nozzle outlet.

18. The aerosol concentration device of claim 17 wherein said acceleration zone is axisymmetric about a central axis the substantially parallel to the principle direction of flow.

19. The aerosol concentration device of claim 17, further comprising a separation zone in liquid communication with the acceleration nozzle.

20. The aerosol concentration device of claim 19, wherein said acceleration zone and said separation zone are each axisymmetric about a central axis the substantially parallel to the principle direction of flow.

21. The aerosol concentration device of claim 19, further comprising a particle collection means downstream from the minor flow outlet.

22. The aerosol concentration device of claim 21, wherein the particle collection means includes a plurality of micro-impactors and other filtration media.

23. The aerosol concentration device of claim 19, wherein said concave section has a minimum radius of curvature $R_{vmin}$, and the convex section has a minimum radius of curvature $R_{xmin}$, such that $R_{vmin}/R_{xmin} \geq 10$.

24. The aerosol concentration device of claim 23, wherein the nozzle outlet has a width of 0.25–5 mm.

25. The aerosol concentration device of claim 24, wherein the fluid inlet to the acceleration nozzle has a width of 1–20 mm.

26. The aerosol concentration device of claim 25, wherein the ratio of the width of the fluid inlet to the acceleration nozzle to the nozzle outlet width is from 4–10.

27. The aerosol concentration device of claim 26, wherein $100 \geq R_{vmin}/R_{xmin} \geq 15$.

28. The aerosol concentration device of claim 26, wherein $35 \geq R_{vmin}/R_{xmin} \geq 20$.

29. A method of concentrating particles contained in a fluid medium, comprising flowing the fluid medium through an aerosol concentration device under conditions such that a minor flow having an increased concentration of particles and at least one major flow having a reduced concentration of particles are produced, wherein the aerosol concentration device includes an acceleration nozzle wherein
1) the acceleration nozzle comprises a conduit which narrows in a principal direction of flow from a fluid inlet into the aerosol concentration device towards the separation zone,
2) the acceleration nozzle includes a concave section in which the interior width of the acceleration nozzle decreases in the principal direction of flow; and
3) the acceleration nozzle includes a convex section downstream of the concave section, wherein the interior width of the acceleration nozzle further decreases in the principal direction of flow and through which the aerosol is directed through a nozzle outlet.

30. The method of claim 29, wherein the aerosol concentration device further comprises a separation zone in liquid communication with the acceleration nozzle, which separation zone includes an inlet from the acceleration nozzle, a minor flow outlet downstream from the acceleration nozzle and oriented substantially along the principle direction of flow; and at least one major flow outlet downstream from the acceleration nozzle and oriented at an angle to the principal direction of flow.

31. The method of claim 29, wherein conditions of flow in the concave section are selected to produce a flow characterized by a Stokes number Stk<0.5 for all particles to be concentrated and collected into the minor flow, wherein $$STK = \frac{\rho_p U d_p^2}{18 \mu D} \tag{I}$$

where $\rho_d$ represents the density of the particle, U represents the local flow velocity in the principle direction of flow, $d_p$ represents the particle diameter, $\mu$ represents the viscosity of the fluid, and D represents the local width or diameter of the conduit.

32. The method of claim 31, wherein the fluid is air, oxygen, nitrogen, argon, carbon dioxide, or water vapor or any combination thereof.

33. The method of claim 32, wherein the aerosol particles include biological matter.

34. The method of claim 33, wherein the biological matter is a pathogen.

35. The method of claim 30, wherein conditions of flow in the convex section are selected to produce a flow characterized by a Stokes number Stk<1.0 for all particles to be concentrated and collected into the minor flow, wherein $$STK = \frac{\partial u/\partial s}{18\mu/\rho_d d_p^2} \quad (II)$$

where ∂u/∂s represents the change in velocity across a streamline, $\rho_d$ represents the density of the particle, $d_p$ represents the particle diameter and μ represents the viscosity of the fluid.

36. The method of claim 35, wherein conditions of flow in the concave section are selected to produce a flow characterized by a Stokes number Stk<0.5 for all particles to be concentrated and collected into the minor flow, wherein $$STK = \frac{\rho_p U d_p^2}{18\mu D} \quad (I)$$

where $\rho_d$ represents the density of the particle, U represents the local flow velocity in the principle direction of flow, $d_p$ represents the particle diameter, μ represents the viscosity of the fluid, and D represents the local width or diameter of the conduit.

37. The method of claim 36, wherein the aerosol particles have a volume average particle diameter of from about 0.5 to about 20 microns.

38. The method of claim 36 wherein the velocity of the fluid flow through the inlet to the separation zone is at least 100 m/s.

39. The method of claim 30, further comprising a particle collection means downstream from the minor flow outlet.

40. The method of claim 39, wherein the fluid is a gas.

41. The method of claim 30, wherein said concave section has a minimum radius of curvature $R_{vmin}$, and the convex section has a minimum radius of curvature $R_{xmin}$, such that $R_{vmin}/R_{xmin} \geq 10$.

42. The method of claim 41, wherein the nozzle outlet has a width of 0.25–5 mm.

43. The method of claim 42, wherein the fluid inlet to the acceleration nozzle has a width of 1–20 mm.

44. The method of claim 43, wherein the ratio of the width of the fluid inlet to the acceleration nozzle to the nozzle outet width is from 4–10.

* * * * *